United States Patent [19]

Ladkani et al.

[11] Patent Number: 4,851,426

[45] Date of Patent: Jul. 25, 1989

[54] ETHOXYCARBONYLOXY ETHYL ESTERS OF NON-STEROIDAL ANTI-INFLAMMATORY CARBOXYLIC ACIDS AND PHARMACEUTICAL COMPOSITIONS THEREOF

[75] Inventors: David Ladkani, Jerusalem; Haim Yellin, Ramat-Gan; Ben Z. Weiner; David Avnir, both of Jerusalem, all of Israel

[73] Assignee: Teva Pharmaceutical Industries, Ltd., Israel

[21] Appl. No.: 810,393

[22] Filed: Feb. 12, 1986

Related U.S. Application Data

[62] Division of Ser. No. 551,028, Nov. 14, 1983, abandoned.

[30] Foreign Application Priority Data

Dec. 9, 1982 [IL] Israel .................................... 674445

[51] Int. Cl.$^4$ ................ C07D 209/28; C07D 207/333; C07C 69/96; A61K 31/405; A61K 31/40; A61K 31/265
[52] U.S. Cl. .................................... 514/420; 514/423; 514/512; 548/500; 548/539; 558/275; 558/276
[58] Field of Search ................ 558/275; 548/500, 539; 514/420, 512, 723

[56] References Cited

U.S. PATENT DOCUMENTS

| | | | |
|---|---|---|---|
| 3,412,131 | 11/1968 | Swintosky | 558/275 |
| 3,646,201 | 2/1972 | Kallianos et al. | 558/275 |
| 4,412,994 | 11/1983 | Sloan et al. | 514/234 |
| 4,426,391 | 1/1984 | Alexander et al. | 558/275 |
| 4,483,867 | 11/1984 | Svehn et al. | 558/275 |
| 4,542,158 | 9/1985 | Dorn | 558/275 |

*Primary Examiner*—David B. Springer
*Attorney, Agent, or Firm*—Steinberg & Raskin

[57] ABSTRACT

Novel esters of the general formula

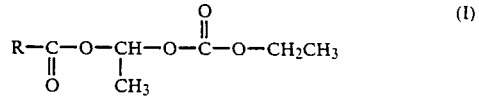

in which

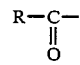

is the acyl residue of a non-steroidal anti-inflammatory compound containing a carboxylic acid function. The novel esters are prepared by reacting an acid R—COOH when R is as above, with 1-haloethyl ethyl carbonate. There are also provided pharmaceutical compositions containing any of the said novel esters.

13 Claims, No Drawings

ETHOXYCARBONYLOXY ETHYL ESTERS OF NON-STEROIDAL ANTI-INFLAMMATORY CARBOXYLIC ACIDS AND PHARMACEUTICAL COMPOSITIONS THEREOF

This is a division of application Ser. No. 551,028, filed 11/14/83, abandoned.

BACKGROUND OF THE INVENTION

The present invention concerns novel ethoxycarbonyloxy ethyl esters of non-steroidal anti-inflammatory substance having a carboxylic acid function, process for their preparation and pharmaceutical compositions containing them.

The novel esters according to the invention are prodrugs of the corresponding non-steroidal anti-inflammatory substances. In the context of the present specification the term "prodrug" denotes a derivative of a known and proven prior art non-steroidal anti-inflammatory substance having a carboxylic acid function such as for example 2-(acetyl)salicyclic acid (Aspirin), compounds known by their generic names indomethacin, ibuprofen, naproxen, diclofenac and the like, which derivatives when administered orally cleave in such a manner as to release the proven anti-inflammatory compound in its carboxylic acid form at its target site or sites of activity. The enzymatic and/or chemical hydrolytic cleavage of the compounds of the present invention occurs in such a manner that the proven drug, i.e. the conventional non-steroidal anti-inflammatory substance is released. The remaining cleaved moiety is non-toxic and is metabolized in such a manner that non-toxic metabolic products are produced such as ethanol, $CO_2$ and acetaldehyde.

It is known that the non-ionized form of a drug is absorbed more efficiently than its ionic species. In the case of non-steroidal anti-inflammatory drugs containing a carboxylic acid function such as those known by the generic names indomethacin, naproxen, ibuprofen, diclofenac and the like the carboxylic acid is significantly ionized at physiological pH. The result is that such non-steroidal anti-inflammatory drugs are poorly absorbed through lipid-water membrane barriers and are irritating to the mucous membrane of the intestinal tract.

Laid open European Patent Application No. 81103066.7, Publication No. 0039051, of Apr. 23, 1981 in the name of Merck and Co. Inc. discloses novel prodrug forms of known non steroidal anti-inflammatory agents have a free carboxylic acid function, which are acetohydroxamic acid derivatives of the formula

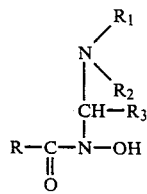

wherein

is the acyl residue of any non-steroidal anti-inflammatory substance containing a carboxylic acid function, $R_1$ and $R_2$ stand for a variety of organic radicals and may also form together with the nitrogen atom to which they are attached a heterocyclic ring, and $R_3$ stands for hydrogen or a variety of organic radicals. However, these prodrugs are of a rather complex nature and are not readily accessible. Thus the process for the preparation of these prodrugs as described in the said European patent application comprises four stages. In the first of these a non-steroidal anti-inflammatory agent having a free carboxylic acid function is converted into the corresponding acid chloride, e.g. by reaction with thionyl chloride. In a second stage the resulting acid chloride is reacted with hydroxyl amine to form a corresponding hydroxamic acid. The latter is then reacted with an aldehyde and the resulting reaction product is reacted with a secondary amine (See pages 14 and 15 of the European patent application).

In addition to the chemical complexity of the prodrug forms of non-steroidal anti-inflammatory substances according to the said European patent application, it is also difficult to predict which of the large variety of acetohydroxamic acid moieties is of sufficiently low toxicity and yields metabolites of sufficiently low toxicity as to be harmless upon cleavage of the prodrug in the body of a mammal.

It is accordingly the object of the present invention to provide novel, improved prodrug forms of known non-steroidal anti-inflammatory substances having a carboxylic function. It is a further object of the present invention to provide non-steroidal anti-inflammatory agents of reduced ulcerogenicity.

It is known from the literature, e.g. from British Patent Specification No. 1,363,506 of Sept. 15, 1971, to convert α-amino penicillins and penicillin G into the corresponding 1'-ethoxycarbonyloxy ethyl esters and it has been found that the absorption of such esters from the intestinal tract is superior to the absorption of a corresponding penicillin in the free acid form. However, the art of anti-bacterial and the antibiotic drugs is different from that of non-steroidal anti-inflammatory agents and the knowledge of the said penicillin esters did not induce people versed in the art of anti-inflammatory agents to look for prodrugs in the form of ethoxycarbonyloxy ethyl esters as manifested by the said European Patent Application No. 81103066.7 which was filed about ten years later.

SUMMARY OF THE INVENTION

In accordance with the present invention it has now surprisingly been found that 1'-ethoxycarbonyloxy ethyl esters of non-steroidal anti-inflammatory substances having a free carboxylic function are excellent prodrug forms of these anti-inflammatory substances possessing increased bioavailability and reduced ulcerogenicity when administered orally as compared to the non-steroidal anti-inflammatory drugs with a free carboxylic function from which they are derived.

The present invention thus provides a novel group of compounds of the general formula

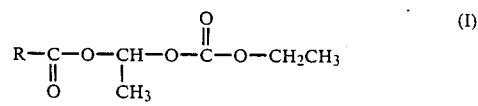

(I)

in which

is the acyl residue of a non-steroidal anti-inflammatory compound containing a carboxylic acid function.

The chemical structure of the non-steroidal anti-inflammatory compounds RCOOH whose acyl residue

is the acyl moiety of the novel esters according to the invention is not critical; non-limiting examples are acetyl salicylic acid (Aspirin), indomethacin, naproxen, ibuprofen, sulindac, diflunisal, ketoprofen, mefenamic acid, tolmetin, diclofenac, flufenamic acid.

On oral administration the esters according to the invention are readily absorbed from the digestive tract and liberate the anti-inflammatory substance in the free carboxylic form in the blood and in this way a high drug concentration is maintained in the blood over long periods of time. This highly advantageous property of the novel esters according to the invention is believed to be due to the fact that while these esters readily undergo enzymatic hydrolysis in-vivo they have a certain resistence to hydrolysis in an aqueous acidic medium. Thus, for example, the 2-ethoxycarbonyloxy ethyl ester of acetyl salicylic acid (Aspirin) is not readily hydrolysed off in aqueous acidic medium (simulated gastric juices) in contrast to the acetyl group of this drug which is readily hydrolysed off under the same conditions. Similarly, the 1'-ethoxycarbonyloxy ethyl ester of salicylic acid is stable in acidic medium.

Likewise the rate of hydrolysis in 0.01N HCl solution at 25° C. of other esters according to the invention was found to be relatively slow (half-life of 32 hours assuming pseudo-first order kinetics). Against this the rate of hydrolysis in-vitro in human plasma was found to be much faster with a half-life of 2.3 hours at 25° C.

These results show that the esters of the present invention are readily hydrolyzed when subjected to the influence of hydrolytic enzymes, for instance such as are present in blood serum, while being relatively resistant to hydrolysis in acidic medium such as the gastric juices. In consequence the release of the active nosteroidal anti-inflammatory substance in the free carboxylic acid form from the prodrug form occurs prior or during absorption processes.

DESCRIPTION OF THE PREFERRED EMBODIMENTS

The novel prodrugs according to the invention are prepared in a simple one-step reaction in which a compound of the general formula

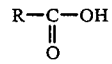 (II)

wherein

has the same meaning as before, or a salt thereof, is reacted with a 1-haloethyl ethyl carbonate of the formula

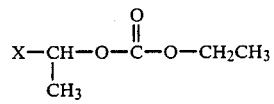 (III)

wherein X represents a halogen atom.

Where a free carboxylic acid is used as starting material for the reaction with 1-haloethyl ethyl carbonate to produce the novel esters according to the invention the reaction is preferably performed in the presence of a base such as for example a trialkylamine, e.g. triethylamine, a metal hydrogen carbonate such as potassium hydrogen carbonate or sodium hydrogen carbonate, or metal carbonates such as sodium and potassium carbonate.

Where a salt is used as starting material the reaction proceeds favourably in the absence of a base.

Preferably, compounds of the above formula III in which X is Cl or Br are used and of these the bromo compounds are particularly preferred. This is so because of the known fact that a C—Br bond is more labile than the C—Cl bond and that in consequence 1-bromoethyl ethyl carbonate is more reactive than the corresponding chloro compound. In consequence the rate of esterification with 1-bromoethyl ethyl carbonate is significantly faster than with a different 1-haloethyl ethyl carbonate, e.g. 1-chloroethyl ethyl carbonate and there is as a rule no need for a large excess of the 1-bromoethyl ethyl carbonate nor are high temperatures and the use of catalysts required. The fact that the esterification with 1-bromoethyl ethyl carbonate proceeds under relatively mild conditions is of particular significance having regard to the sensitivity of some of the non-steroidal anti-inflammatory substance in the free carboxylic acid form whose ester prodrugs are produced in accordance with the present invention.

1-Bromoethyl ethyl carbonate is a novel compound and the fact that this compound was hitherto unavailable may have contributed to the fact that the novel prodrug esters according to the invention have hitherto not been produced although there had existed a long-felt want for readily accessible and effective prodrugs of non-steroidal anti-inflammatory substances.

1-Bromoethyl ethyl carbonate can be produced by brominating diethyl carbonate with elementary bromine or a brominating agent, e.g. 1,3-dibromo-5,5-dimethylimidazolidine-2,4-dione, in an aprotic inert solvent and under conditions conducive of free radical formation, the amount of bromine made available in the bromination being not more than the stoichiometric quantity. For free radical initiation it is possible to use light or free radical initiator such as, for example, azobisisobutyronitrile.

The invention is illustrated by the following examples without being limited thereto:

EXAMPLE 1

Production of 1-bromoethyl ethyl carbonate

A mixture of 195 g diethylcarbonate and 500 ml of 1,1,2-trichlorotrifluoroethane was irradiated externally by a 1.5 kw iodine-quartz lamp. The mixture soon refluxed by the heat evolved from the lamp. The temperature in the flask was 60° C. 79.0 g of 1,3-dibromo-5,5-dimethylimidazoline-2,4-dione was added in small portions during 6 hours. The mixture was irradiated and refluxed for another 20 minutes and cooled. Solids were removed by filtration. The solution was fractionally distilled first at atmospheric pressure and then under vacuum. 1-Bromoethyl ethyl carbonate was distilled at 91° at 20 mm Hg pressure. The fraction weighed 60 g and was shown to be 98% pure, by GC.

The following are physical data of 1-bromoethyl ethyl carbonate:

| | |
|---|---|
| Boiling point at 60 mm Hg - 110° | |
| Bromine content 40.6% (theoretical 40.61%) | |
| Density ($D_4^{20}$) | 1.4244 |
| Refraction index ($n_D^{20}$) | 1.4395 |
| NMR Spectrum: | 1.4 ppm 3H triplet J = 7 Hz |
| | 2.0 ppm 3H doublet J = 6 Hz |
| | 4.25 ppm 2H quartet J = 7 Hz |
| | 6.6 ppm 1H quartet J = 6 Hz |

EXAMPLE 2

The preparation of 1'-ethoxy carbonyloxy ethyl ester of 2-(acetyloxy)benzoic acid (Aspirin)

Anhydrous potassium carbonate (0.3 equivalent) was added to a solution of 2-(acetyloxy)benzoic acid (Aspirin) (0.12 mole) in acetone. To the mixture, 1.2 mole of 1-bromoethyl ethyl carbonate was added and the mixture was heated for 3 hours at reflux. The cooled mixture was poured into water and stirred for 1 hour, at room temperature. The organic phase was separated, the aqueous phase extracted with methylenechloride and the combined organic phases washed with water and dried over $MgSO_4$. A pure oily product was obtained in 80% yield after evaporation of the methylene chloride.

| | | | |
|---|---|---|---|
| IR (neat): 1760 and 1740 cm$^{-1}$ (s) (O—C—O and —C—O) | | | |
| | || O || O | | |
| NMR, δ(CDCl$_3$): | 8.15–7.4 (4H, multiplet) | | Aromatic |
| | 7.15 (1H, AB quartet) | | CH$_3$—C̲H̲—O |
| | 4.3 (2H, AB quartet) | | CH$_3$—C̲H̲$_2$—O |
| | 2.35 (3H, s) | | C̲H̲$_3$CO |
| | 1.6 (3H, d) | | C̲H̲$_3$—CHO |
| | 1.35 (3H, t) | | C̲H̲$_3$—CH$_2$—O |
| Anal. calcd. for | C$_{14}$H$_{16}$O$_7$ | (m.w. 296) | |
| C | 56.76 | H | 5.41 |
| found C | 56.63 | H | 5.31 |

EXAMPLE 3

The preparation of 1'-ethoxy carbonyloxy ethyl ester of salicyclic acid

Equimolar quantities (0.072 mole) of salicylic acid (10 g), NaHCO$_3$ (7.1 g) and 1-chloroethyl ethyl carbonate were added to 70 ml DMSO.

The mixture was stirred at room temperature, until no starting material could be detected (TLC). The mixture was poured into water, stirred for 1 hour and then extracted with CH$_2$Cl$_2$. The organic layer was separated, washed with NaHCO$_3$ solution, then with water and dried over MgSO$_4$. The oily residue obtained after evaporation of CH$_2$Cl$_2$ contained traces of unreacted 1-chloroethyl ethyl carbonate, DMSO and the product. Column chromatography on silica with CH$_2$Cl$_2$ afforded 8 g (41%) pure colourless oily product.

Better yields were obtained by reacting directly sodium salicylate with 1-bromoethyl ethyl carbonate.

IR (neat) 1765 and 1745 cm$^{-1}$ (s).

NMR, δ(CDCl$_3$): 7.33 (6H, m, Ar+OH+CH$_3$CHO), 4.16 (2H, q, OCH$_2$CH$_3$), 2.26 (3H, d, CH$_3$CHO), 1.26 (3H, t, CH$_3$CH$_2$O).

By following the procedure of the foregoing examples several more novel esters according to the invention of non-steroidal anti-inflammatory substances were prepared. In the following Examples 4 to 13 only the generic and chemical designations, the structural formulae and the physical properties of the products are given. In the generic and designation and structural formulae the abbreviation ECOE is used for the ethoxycarbonyl ethyl moiety.

EXAMPLE 4

1-(p-Chlorobenzoyl)-5-methoxy-2-methylindole-3-acetic acid 1'-ethoxycarbonyloxy ethyl ester

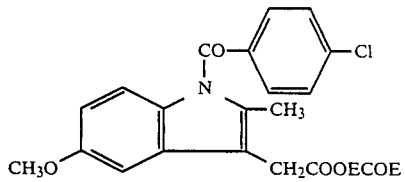

Indomethacin—ECOE ester.
Solid, melting point 86.7° C. (isopropanol hexane).
IR cm$^{-1}$: 1760, 1740.
NMR δ, in CDCl$_3$: 7.6 6.4 (8H, m, Ar+CH$_3$—CHO), 4.0 (2H, q, CH$_3$—CH$_2$—O), 3.7 (3H, s, CH$_3$O), 3.6 (2H, s, CH$_2$CO), 2.25 (3H, s, CH$_3$CO), 1.5 (3H, d, CH$_3$—CH), 1.2 (3H, t, CH$_3$CH$_2$).

EXAMPLE 5

(+)-6-Methoxy-α-methyl-2-naphthaleneacetic acid 1'-ethoxycarbonyloxy ethyl ester

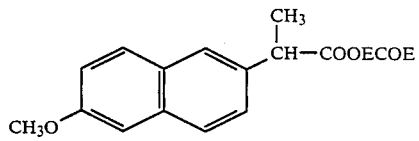

Naproxen—ECOE ester.
Oil at room temperature.
IR cm$^{-1}$: 1760, 1740.
NMR δ, in CDCl$_3$ 300M H$_z$: 7.67–7.12 (6H, Ar), 6.78 (1H, 2q, CH$_3$CHO), 4.18 (2H, q, CH$_2$CH$_3$), 3.85, 3.97 (1H, 2q, CH$_3$CHCO), 3.87 (3H, s, CH$_3$O), 1.57 (3H, d, CH$_3$CH), 1.48, 1.38 (3H, d, CH$_3$CH), 1.27, 1.21 (3H, t, CH$_3$CH$_2$O).

EXAMPLE 6

α-Methyl-4-(2-methylpropyl)benzene—acetic acid 1'-ethoxycarbonyloxy ethyl ester

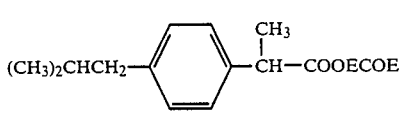

Ibuprofen—ECOE ester.
oil at room temperature.
IR cm$^{-1}$: 1760, 1740.

| NMR δ, in CDCl$_3$ | 300 M Hz |
|---|---|
| | 7.18–7.06 (4H, q + d, Ar) |
| | 6.75 (1H, 2q, CH$_3$CH—O) |
| | 4.19, 4.09 (2H, 2q, CH$_3$CH$_2$O) |
| | 3.69 (1H, 2q, CH$_3$CH) |
| | 2.43 (2H, 2d, CH$_2$—CH⟨ ) |
| | 1.85 (1H, Septet, CH⟨ ) |
| | 1.47, 1.44 (6H, 2d + d, CHCH$_3$; OCHCH$_3$) |
| | 1.30, 1.25 (2H, 2t, CH$_3$CH$_2$) |
| | 0.88 (6H, d, (CH$_3$)$_2$CH) |

EXAMPLE 7

2-[(2,6-Dichlorophenyl])amino]benzene-acetic acid 1'-ethoxycarbonyloxy ethyl ester

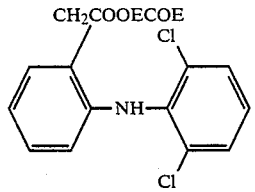

Diclofenac—ECOE ester.
Solid, melting point 57° C. (MeOH).
IR cm$^{-1}$: 1765, 1750.
NMR δ, in CDCl$_3$: 7.28 (8H, Ar+CH$_3$CHO, NH), 4.2 (2H, q, CH$_3$CH$_2$O), 3.8 (2H, s, OCH$_2$CH$_3$), 1.5 (3H, d, CH$_3$CHO), 1.3 (3H, t, CH$_3$CH$_2$O).

EXAMPLE 8 m-Benzoylhydratropic acid 1'-ethoxycarbonyloxy ethyl ester

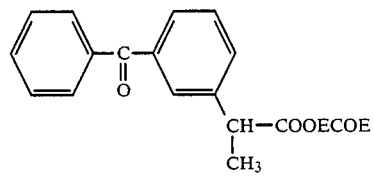

Ketoprofen—ECOE ester.
Oil at room temperature.
IR cm$^{-1}$: 1765, 1735.
NMR δ, in CDCl$_3$: 7.52 (9H, m, Ar), 6.70 (1H, q, CH$_3$CHO—), 4.09 (2H, 2q, CH$_3$CH$_2$O), 3.76 (1H, 2q, CH$_3$CHCO), 1.53 (3H, d, CH$_3$CHO), 1.40 (3H, d, Me), 1.33 (3H, t, Me).

EXAMPLE 9

2-[(2,3-Dimethylphenyl)amino]-benzoic acid 1'-ethoxycarbonyloxy ethyl ester

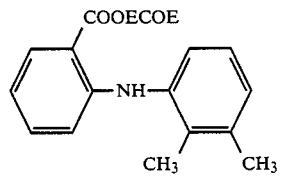

Mefenamic Acid—ECOE ester.
Oil at room temperature.
IR cm$^{-1}$: 3320, 1755, 1745.
NMR δ, in CDCl$_3$: 9.13 (1H, br.s, NH), 7.96 (1H, d, ortho H to coAr), 7.1 (6H, m, Ar+); 6.66 (1H, q, CH$_3$CHO), 4.23 (2H, q, CH$_2$CH$_2$O), 2.29 (3H, s, Me), 2.13 (3H, s, Me), 1.69 (3H, d, CH$_3$CH), 1.33 (3H, t, CH$_3$CH$_2$O).

EXAMPLE 10

(Z)-5-Fluoro-2-methyl-1-[[4-(methylsulfinyl)-phenyl]-methylene]-1H-indene-3-acetic acid 1'-ethoxycarbonyloxy ethyl ester

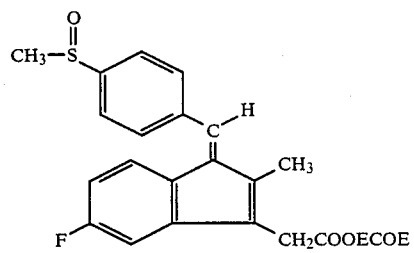

Sulindac—ECOE ester.
Oil at room temperature.
IR cm$^{-1}$: 1760, 1745.
NMR δ, in CDCl$_3$: 7.6 (3H, s, Ar) H, 7.25–6.25 (6H, m, Ar=C=C+CH$_3$CHO), 4.15 (2H, q, CH$_3$CH$_2$O), 3.55 (2H, s, CH$_2$CO), 2.75 (3H, s, Me), 2.20 (3H, s, Me), 1.50 (3H, d, CH$_3$CH$_2$), 1.25 (3H, t, CH$_3$CH$_2$).

EXAMPLE 11

2-[[3-(Trifluoromethyl)phenyl]-amino]benzoic acid 1'-ethoxycarbonyloxy ethyl ester

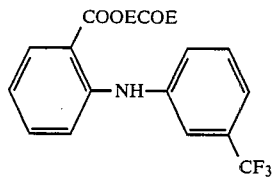

Flufenamic Acid—ECOE ester.
Oil at room temperature.
IR cm$^{-1}$: 3320, 1755, 1745.
NMR δ, in CDCl$_3$: 9.42 (1H, br.s, NH), 7.93 (1H, d, H ortho to CO), 7.03 (8H, m, Ar+CH$_3$CHO), 4.20 (2H, q, CH$_3$CH$_2$O), 1.66 (3H, d, CH$_3$CHO), 1.26 (3H, t, CH$_3$CH$_2$O).

EXAMPLE 12

1-Methyl-5-(α-methylbenzoyl)-1H-pyrrole-2-acetic acid 1'-ethoxycarbonyloxy ethyl ester

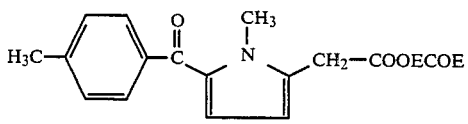

Tolmetin—ECOE ester.
Oil at room temperature.
IR cm$^{-1}$: 1765, 1740.
NMR δ, in CDCl$_3$: 7.49 (4H, ABq, Ar), 6.82 (1H, q, CH$_3$CHO), 6.42 (2H, ABq, Pyrrole H), 4.23 (2H, q, CH$_3$CH$_2$O), 3.93 (3H, s, Me), 3.60 (2H, s, CH$_2$CO), 2.43 (3H, s, ArMe), 1.59 (3H, d, CH$_3$CHO), 1.33 (3H, t, CH$_3$CH$_2$O).

The proton, IR, UV and mass spectra and the elemental analyses of all the above esters were in accord with the molecular structure.

In each case where optically active non-steroidal anti-inflammatory carboxylic acids were used the NMR spectrum (300 MH$_z$) of the corresponding ethoxy carbonyloxy ethyl ester showed existence of a diasteroisomeric mixture.

The rates of hydrolysis of 2-(acetyloxy)benzoic acid (Aspirin) ethoxy carbonyloxy ethyl ester to salicylethoxy carbonyloxy ethyl ester in the aqueous acidic medium (simulated gastro-intestinal juices) were determined by dissolving the ester to a pre-determined concentration in the acidic medium containing THF: aqueous conc. HCl=1:1 and the rate of hydrolysis at 37° C. was measured by the HPLC method. The results are given in the following table:

| Time (Min.) | Ester (%) |
| --- | --- |
| 0 | 100 |
| 30 | 96 |
| 60 | 92 |
| 90 | 90 |
| 120 | 90 |
| 150 | 84 |
| 180 | 82 |
| 210 | 76 |

The rate of hydrolysis of salicyclic acid 2-ethoxycarbonyloxy ethyl ester under the same experimental conditions was determined in a similar way and this ester was found to be stable.

These results show that the 2-ethoxy carbonyloxy ethyl esters of non-steroidal anti-inflammatory substances according to the invention are relatively stable against hydrolysis in acidic medium. Thus, they are generally adsorbed from the gastro-intestinal tract to the blood system in the ester form.

From pharmacokinetic data it was further found that the novel esters according to the invention exhibit characteristics of slow release profile.

PHARMACOLOGICAL TESTS

The anti-inflammatory and analgesic activities of the prodrugs of formula (A), as well as their reduced ulcerogenicity and improved bioavailability in comparison with parent non-steroidal anti-inflammatory drugs are evident from the results of the tests obtained with representative compounds of the invention. Details of these tests and results are given thereafter.

1. Anti-Inflammatory Activity

Test Procedures (a) Carrageenin-oedema Test

1. Prior to administration of test materials and reference compounds, the volume of the right hind paw to the level of the lateral malleolus in all test animals (pre-injection paw volume) was measured with an Hg-displacement volumeter (Hugo Basile, Italy).

II. Test materials and reference compounds, suspended in 0.5% CMC at concentrations appropriate to selected dose levels were administrated at a constant volume-dosage of 10 ml/kg by oral gavage with a flexible catheter (choke 8) passed down the oesophagus into the lumen of the stomach.

III. One hour after administration, 0.1 ml of 1% carrageenin suspended in 0.9% sterile saline solution was injected subcutaneously into the sole of the right hind paw.

IV. Volume of the injected foot (i.e. oedema intensity) was determined at 1 and 3 hours after carrageenin injection as detailed above in paragraph 1.

Evaluation of Data

Carrageenin-oedema Test

The intensity of oedema, expressed as percent increase in the injected foot volume was calculated for each treatment and the control group, by the following equation:

(Mean post-injection volume—mean pre-injection volume)×100/mean pre-injection volume.

Anti-inflammatory activity was expressed as percent-inhibition of oedema, which in turn was calculated for each treatment group by the following equation:

(Mean percent-increase paw volume of controls—mean percent increase paw volume of treated)×100/mean percent increases paw volume of controls.

TABLE 1

Comparative prophylactic anti-inflammatory activity of test materials, assessed by inhibition of oedema in the carrageenin-induced rat-paw oedema test

| Treatment* | Dosage mg/kg p.o. | No. of animals | % inhibition of aedema** 3 hrs*** | % activity vs. parent compound |
|---|---|---|---|---|
| Indomethacin | 5.0 | 6 | 65.1 | |
| Indomethacin-ECOE ester | 6.6 | 6 | 65.1 | 100 |
| Diclofenac | 4.0 | 6 | 39.3 | 100– |
| Diclofenac-ECOE ester | 5.6 | 6 | 34.6 | 88 |
| Acetylsalicylic acid | 100.0 | 6 | 31.4 | |
| Acetylsalicylic acid-ECOE ester | 164.0 | 6 | 20.2 | 64.24 |
| Ibuprofen | 25.0 | 6 | 44.7 | 100– |
| Ibuprofen-ECOE ester | 39.0 | 6 | 48.9 | 107.59 |
| Naproxen | 20.0 | 6 | 20.2 | 100– |
| Naproxen-ECOE ester | 30.0 | 6 | 28.0 | 138.9 |

* All test materials were administered 1 hour before carrageenin.

** $\dfrac{\text{Mean \% incr. paw vol. of controls} - \text{Mean \% incr. paw vol. of treated}}{\text{Mean \% incr. paw vol. of controls}} \times 100$

***After sub-plantar injection of 1% carrageenin.

(b) Adjuvant arthritis (chronic inflammation)

Adjuvant arthritis test

I. Arthritis was induced by subplantar injection into the right hind paw of 0.1 ml of Killed Mycobacterium butyricum, suspended at a concentration of 5 mg/ml in liquid paraffin. On Day 21 after subplantar injection, only those animals which clearly developed signs of arthritis were selected and divided by random order into treatment groups.

II. Test materials and reference compounds, suspended in 0.5% CMC at concentrations appropriate to selected dose levels, and CMC only for adjuvant-control animals, were administered once daily for 10 consecutive days (i.e. starting on Day 21 after subplantar injection of adjuvant until Day 30). Administration was by oral gavage with a flexible catheter introduced via the oesophagus into the lumen of the stomach. Volume in all cases was 10 ml/kg.

III. Swellings of the injected hind paws were measured on Day 31 with a micrometer, across a sagittal section of the matatarsus just below the tarsus.

Evaluation of Data

The comparative therapeutic anti-inflammatory activity of the test materials and reference compounds was expressed as percent inhibition of swelling in injected pawa after 10 days of treatment (i.e. 31 days after adjuvant injected) in comparison to the non-treated adjuvant-controls. Percent inhibition for each treatment group was calculated by the following equation:

(Mean paw swelling of control — mean paw swelling of treated) × 100/mean paw swelling of control.

TABLE 2

Results: Comparative therapeutic anti-inflammatory activity of test materials, assessed by inhibition of swelling in the adjuvant-injected rat-paw oedema test.

| Treatment* | Dosage mg/kg p.o. | No. of animals | Mean paw swelling** | % inhibition of swelling compared to controls |
|---|---|---|---|---|
| Adjuvant Control (0.5% CMC)*** | — | 18 | 15.3 | — |
| Indomethacin | 2.0 | 5 | 10.1 | 34.0 |
| Indomethacin-ECOE ester | 2.6 | 5 | 9.9 | 35.3 |
| Diclofenac | 2.0 | 5 | 10.0 | 34.6 |
| Diclofenac-ECOE ester | 2.8 | 5 | 10.9 | 28.8 |
| Acetylsalicylic acid | 200.0 | 5 | 11.8 | 22.9 |
| Acetylsalicylic acid-ECOE ester | 330.0 | 5 | 12.4 | 19.0 |
| Ibuprofen | 60.0 | 5 | 10.3 | 32.8 |
| Ibuprofen-ECOE ester | 94.0 | 5 | 10.4 | 32.0 |
| Naproxen | 10.0 | 5 | 10.1 | 34.0 |
| Naproxen-ECOE ester | 15.1 | 5 | 10.9 | 28.8 |

*Administered by daily oral gavage during 10 consecutive days at a volume dosage of 10 ml/kg.
**Measured after termination of 10 day treatment (Day 31), expressed as mm units read off micrometer.
***Carboxymethylcellulose in 2 × distilled H₂O.

2. Analgesic Action

Test Animals

Male rats, weighing 95–140 g, 10 rats per experimental group. The major reason for selecting rats of this weight range is the ease in handling smaller sized animals in this particular test. Animals are fed and provided drinking water ad libitium until time of testing.

Procedure

A—Inflammation is induced by injecting subcutaneously 0.1 ml of a 20% suspension of brewers' yeast in saline into the plantar surface of the right hand paw of the rat. (Note: Brewers' yeast, locally obtainable from "Abir" breweries, may be kept under refrigeration for a period of at least 6 months).

B—One hour after sub-plantar injection of brewers' yeast, the experimental compound, customarily dissolved in 1% TWEEN-80, is orally administered to rats usually at a standard dose-volume of 0.5 ml/100 g body weight.

C—At 1, and 3 hours after administration of the test substance on the vehicle, the experimental or control animals, respectively, are tested for determining their reaction threshold to pressure applied to the inflamed foot by employing the Basile-Analgesy-Meter. This instrument is basically a device which exacts force that increases at a constant rate (a certain number of grams per second). The force of pressure required to produce the typical escape response, exhibited by the animal as a noticeable struggle to withdraw the inflamed foot (sometimes accompanied by vocalization), is read off the instrument's scale and recorded.

Note: In case weight discs are being used to increase the force of pressure applied, the same number of discs should be employed throughout the entire experiment for both experimental and control animals. For detailed operation of the analgesy-meter reference to the specific instructions of the instrument given in the appendix.

Calculation of Results a. The results of the recoreded Pressure Reaction Thresholds (measured on the analgesy-meter scale calibrated in grams × 10) expressed as grams, are calculated a Mean Group Values±S.E.M. for each test group and testing period, i.e. 1, and 3 hours after test substance or vehicle administration.

b. The differences in the various Mean Group Values between treatment and control group are analyzed for statistical significance using the Student t-Test.

TABLE 3

| Compound | Results: | | | |
|---|---|---|---|---|
| | % of control 1 hr | % of control 3 hrs | % effect vs. parent compound 1 hr | % effect vs. parent compound 3 hrs |
| Control TWEEN | 100 | 100 | — | — |
| Indomethacin | 128 | 146 | — | — |
| Indomethacin-ECOE ester | 130 | 153 | 102 | 105 |
| Aspirin | 126 | 100 | — | — |
| Aspirin-ECOE ester | 178 | 148 | 141 | 150 |
| Diclofenac | 123 | 133 | — | — |
| Diclofenac-ECOE ester | 106 | 110 | 86 | 82 |
| Ibuprofen | 152 | 145 | — | — |
| Ibuprofen-ECOE ester | 176 | 129 | 115 | 89 |
| Naproxen | 116 | 133 | — | — |
| Naproxen-ECOE ester | 125 | 121 | 108 | 91 |

3. Ulcerogenicity

Methods: Six groups of 10 female Charles River rats weighing 170–230 g were used for each drug. Rats were fasted for a 24 hour period prior to experimentation, but were allowed free access to water during this period. Drugs were freshly suspended in water with 1% carboxymethyl cellulose and administered by stomach tube. Rats treated were sacrificed 5 hours after oral gavage. Ulcers were evaluated under a magnifying lens, after the stomach had been dissected out, opened along the lesser curvature and rinsed.

Ulcer index (UI) for each group was calculated as the mean sum of the lengths of the individual lesions in each rat.

Apparent maximal ulcerogenicity was calculated from regression analysis of the ascending parts of each dose-response curve.

TABLE 4

| Compound | Results: | | | | |
|---|---|---|---|---|---|
| | Slope[5] Uxkg/mmole | $UD_{50}$[4] mmole/kg | $UI_{50}$[3] | $UD^2$max mmole/kg | $UI^1$ max |
| Acetyl salicylic acid | 33.7 ± 11.5 | 0.02 | 46.3+ | 0.4 | 92.6 |
| Acetyl salicylic acid-ECOE ester | 13.7 ± 6.5 | 0.02 | 20.5+ | 0.4 | 40.9 |
| Ibuprofen | 38.1 ± 8.0 | 0.325 | 26.0 | 2.8 | 52.0 |
| Ibuprofen-ECOE ester | 36.7 ± 8.5 | 0.300 | 13.0 | 0.7 | 26.0 |
| Indomethacin | 50 | — | — | 0.32 | 60 |
| Indomethacin-ECOE ester | 34 ± 13.8 | — | — | 0.32 | 42.0 |
| Diclofenac | 31.1 ± 8.7 | — | — | 0.6 | 61.8 |
| Diclofenac-ECOE ester | 21.1 | — | — | 0.6 | 34.9 |
| Naproxen | 41.0 ± 14.2 | 0.17 | 31.0+ | 2.0 | 62.0 |
| Naproxen-ECOE ester | 63.5 ± 0.59 | 0.59 | 32.5+ | 1.0 | 65.0 |

+ doese response curve aquired bell shape
— no plateau reached
UI max - ulcerogenic index max
UD max - dose causing max ulcerogenic index
$UI_{50}$ - 50% of ulcerogenic index max
$UD_{50}$ - dose causing $DII_{50}$ 4. Bioavailability-pharmacokinetic profile in rats of ECOE ester of acetyl salicylic acid Methods: Female Charles River rats weighing 200–250 g were used. Rates were starved for a 24 hour period prior to each experiment, while water was allowed ad libitum. Aspirin or aspirin ECOE ester was freshly suspended in water with 1% carboxymethyl cellulose and administered by stomach tube at a dose of 0.4 mmole/kg.

Blood was drawn from the tail at 0, ½, 1, 2 and 4 hours in one group, and at 0, 4, 6, 8, 12 and 24 hours in another group of rats. Plasma salicylate concentrations were measured by fluorometry according to Frey and El-Sayed (Arch. Int. Pharmacodyn. 230: 300, 1977). The assay was found to be specific for salicylate and to exclude aspirin or aspirin derivative.

Statistical evaluation was effected by (unpaired) Student t test.

Results and Discussion

As FIG. 5 shows, plasma concentrations of salicylate quickly after aspirin had peaked at 121.3 7.9 g/ml after 1 hour, while the ascent after the derivative was more gradual, to reach a peak of 97.9 5.5 only after 4 hours. Thereafter, the salicylates concentrations did not differ significantly in the two groups. The areas under the plasma concentration-time curves were, however, not significantly different between the two groups neither at 0–4 hours (293.9±18.1 g/ml. hour for the derivative vs 373.3±52.9 for aspirin), nor at 4–24 hours (1440.6±67.0 for the derivative vs 1553.3±161.2 for aspirin).

From the above results one may conclude that aspirin ECOE ester acts as a prodrug and releases salicylate in rat plasma. Although the rate of appearance of salicylate seems slower after the oral gavage of the derivative than of plain aspirin, the bioavailability of salicylate from the derivative preparation seems complete. The slower build-up of salicylate levels may be related either to slower gastrointestinal absorption of the derivative or slower hydrolysis, or both. In view of the much smaller ulcerogenic liability of the derivative and considering its fair bioavailability as presently shown, aspirin ECOE ester seems to have significant advantages over Aspirin itself.

5. Hydrolysis

The rates of hydrolysis of acetyl salicylic acid ethoxy carbonyloxy ethyl ester to salicyl-ethoxy carbonyloxy ethyl ester in aqueous acidic system (simulated gastrointestinal juices) are given in the following table:

| Hydrolysis of Aspirin ester to Salicyl ester | |
|---|---|
| TIME (Min.) | ESTER (%) |
| 0 | 100 |
| 30 | 96 |
| 60 | 92 |
| 90 | 90 |
| 120 | 90 |
| 150 | 84 |
| 180 | 82 |
| 210 | 76 |

Ethoxy carbonyloxy ethyl ester of Aspirin was dissolved to a predetermined concentration in an acidic aqueous medium (simulated gastric juice)—mixture THF; aqueous conc. HCl (1:1) and the rate of hydrolysis at 37° C. was measured by HPLC method.

Salicyl 2-ethoxy carbonyloxy ethyl ester in the same experimental conditions was found to be stable.

| Stability of Salicyl - 2-Ethoxy carbonyloxy ethyl ester | |
|---|---|
| TIME (Min.) | ESTER (%) |
| 0 | 100 |
| 150 | unchanged |
| 180 | unchanged |
| 210 | unchanged |
| 240 | unchanged |

The results of all the above tests can be summarized as follows:

The 2-ethoxy carbonyloxy ethyl esters of non-steroidal anti-inflammatory drugs, the compounds of the present invention, have shown to possess a high degree of anti-inflammatory and analgesic activity with low toxicity, especially being less ulcerogenic than the parent acids, but retain their anti-inflammatory acitivity.

The compounds of the present invention are conveniently administered to warm-blooded animals by conventional oral or topical administration. The ECOE esters of non-steroidal anti-inflammatory substances which are usually in the crystalline form, can be conveniently combined with any suitable non-toxic pharmaceutically acceptable oral inert carrier materials to form tablets or capsules. Such carrier materials are well known to those skilled in the art of oral pharmaceutical formulations. Those ECOE esters which are in a liquid form can be conveniently incorporated in soft-gelatine capsules as is well known to those skilled in the art, or be prepared in solution form.

Similarly, any one of the compounds of the invention can be combined with a topical vehicle, such as triacetin, so that the active ingredient is present in an effective amount. Such a preparation in the form of ointment, cream or jelly is applied topically to the inflamed area, whereby the therapeutically active compound is dermally absorbed and cleared to release the parent moiety at the site of inflammation.

The therapeutic dosage range for the compounds of the invention will vary with the size and needs of the patient. However, generally the therapeutic oral dose of the compound of the present invention, mimic, on a molecular basis, that dose of the parent-conventional nonsteroidal anti-inflammatory moiety (e.g. aspirin, indomethacin, naproxen, etc.).

For topical application, a 0.1% to 2.5% concentration of a compound of the present invention in a suitable topical carrier to the site of inflammation is sufficient. The compounds of the present invention are well absorbed percutaneously and consequently are by far more potent topically than the parent substance as they are poorly absorbed percutaneously.

The compounds of the present invention are all lipid-soluble products. They are soluble in all conventional organic solvents including light petroleum-ether. Topical application of the said compounds have produced a higher anti-inflammatory potency than that of the parent compounds from which they are derived. They penetrate easily through skin, and hydrolyse enzymatically to release the parent non-steroidal anti-inflammatory agent at the target organ and bring to fast relief of the rheumatic pains.

We claim:

1. Ester of the formula:

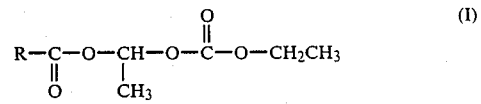

in which

is the acyl residue of a non-steroidal anti-inflammatory compound containing a carboxylic acid function and at least one aromatic ring and being selected from the group consisting of 1-(p-chlorobenzyl)-5-methoxy-2-methylindole-3-acetic acid, (+)-6-methoxy-α-methyl-2-naphthaleneacetic acid, α-methyl-4-(2-methylpropoyl)benzene-acetic acid, 2-((2,6-dichlorophenyl)amino)benzene-acetic acid, m-benzoylhydratropic acid, 2-((2,3-dimethylphenyl)amino)-benzoic acid, (Z)-5-fluoro-2-methyl-1-((4-methylsulfinyl)methylene)-1H-indene-3-acetic acid, 2-((3-(trifluoromethyl)phenyl)-amino)benzoic acid and 1-methyl-5-(α-methylbenzoyl)-1H-pyrrole-2-acetic acid.

2. Ester of claim 1 being 1-(p-Chlorobenzoyl)-5-methoxy-2-methylindole-3-acetic acid 1'ethoxycarbonyloxy ethyl ester.

3. Ester of claim 1 being (+)-6-Methoxy-α-methyl-2-naphthaleneacetic acid 1'-ethoxycarbonyloxy ethyl ester.

4. Ester of claim 1 being α-Methyl-4-(2-methylpropyl)benzene-acetic acid 1'-ethoxycarbonyloxy ethyl ester.

5. Ester of claim 1 being 2-(2,6-Dichlorophenyl)amino)benzene-acetic acid 1'-ethoxycarbonyloxy ethyl ester.

6. Ester of claim 1 being m-Benzoylhydratropic acid 1'-ethoxycarbonyloxy ethyl ester.

7. Ester of claim 1 being 2-((2,3-Dimethylphenyl)amino)-benzoic acid 1'-ethoxycarbonyloxy ethyl ester.

8. Ester of claim 1 being (Z)-5-Fluoro-2-methyl-1-((4-methylsulfinyl)-phenyl)methylene)-1H-indene-3-acetic acid 1'-ethoxy-carbonyloxy ethyl ester.

9. Ester of claim 1 being 2-((3-(Trifluoromethyl)-phenyl)-amino)benzoic acid 1'-ethoxycarbonyloxy ethyl ester.

10. Ester of claim 1 being 1-Methyl-5-(α-methylbenzoyl)-1H-pyrrole-2-acetic acid 1'-ethoxycarbonyloxy ethyl ester.

11. A pharmaceutical composition comprising an anti-inflammatory effective amount of a compound according to claim 1 together with a pharmaceutically suitable carrier.

12. A pharmaceutical composition according to claim 11 adapted for oral administration.

13. A pharmaceutical composition according to claim 11 adapted for topical application.

* * * * *